United States Patent [19]

Shepherd

[11] Patent Number: 4,526,970
[45] Date of Patent: Jul. 2, 1985

[54] PREPARATION OF TETRAHYDROQUINOLINES AND RELATED COMPOUNDS

[75] Inventor: Robin G. Shepherd, Maidenhead, England

[73] Assignee: John Wyeth & Brother Limited, Maidenhead, England

[21] Appl. No.: 506,279

[22] Filed: Jun. 21, 1983

[30] Foreign Application Priority Data

Jun. 25, 1982 [GB] United Kingdom ............... 8218465

[51] Int. Cl.³ ............... C07D 215/16; C07D 219/04; C07D 221/06; C07D 221/16
[52] U.S. Cl. ............................. 546/169; 546/93; 546/102; 546/104; 546/176; 546/79
[58] Field of Search ............... 546/79, 93, 176, 102, 546/104, 169

[56] References Cited

U.S. PATENT DOCUMENTS 4,000,278 12/1976 Curran .................................. 546/93
4,085,108 4/1978 Curran et al. ....................... 546/79

FOREIGN PATENT DOCUMENTS 1432378 9/1973 United Kingdom .
1463665 11/1974 United Kingdom .
1463666 12/1974 United Kingdom .
1463668 3/1975 United Kingdom .
1465651 4/1975 United Kingdom .
1495993 1/1976 United Kingdom .

OTHER PUBLICATIONS

CA 95:81085t.
CA 96:6242j (1982).
CA 81:153382y (1974).
CA 90:87566u (1979).

Chem. Abstracts, vol. 83, (1975), p. 473, Abstract No. 27828b.
Chem. Abstracts, vol. 85, (1976), p. 506, Abstract No. 46340u.

Primary Examiner—Donald G. Daus
Assistant Examiner—William A. Teoli, Jr.
Attorney, Agent, or Firm—Richard K. Jackson

[57] ABSTRACT

An improved process for preparing tetrahydroquinolines and related compounds especially 5,6,7,8-tetrahydroquinoline-8-nitriles, amides and thioamides is described. The nitriles and thioamides are anti-ulcer and/or anti-secretory agents. Typically a compound of formula A

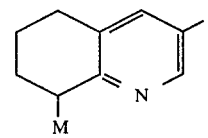

where M is sodium, potassium, lithium or MgHal where Hal is chlorine, bromine or iodine, is reacted, e.g., in an ether solvent, with a silyl compound $R_x{}^a Si(NCY)_{4-x}$ (III) wherein $R^a$ is alkyl, cycloalkyl, aralkyl, or aryl, at least one group $R^a$ being a branched chain alkyl, cycloalkyl, aryl or branched chain aralkyl, Y is oxygen or sulphur, x has a value from 1 to 3, then subjecting the product to hydrolysis or alcoholysis, to obtain the corresponding nitrile, amide or thioamide, provided that when a nitrile is desired the molar ratio of compound III to compound A is at least 2:1 and x is 3 and Y is S. The products may be obtained as acid addition salts.

Compound A may contain various substituents, e.g., hydrocarbon substituents. Some compounds of formula III are novel and are also claimed.

12 Claims, No Drawings

PREPARATION OF TETRAHYDROQUINOLINES AND RELATED COMPOUNDS

The invention relates to a new process for preparing fused carbocyclic ring derivatives of pyridine and to novel silyl reagents used in the process.

In our United Kingdom Specification No. 1463666 we described a process for preparing tetrahydroquinoline-8-thiocarboxamides, nitriles and carboxamides and related compounds by treating a corresponding sodio, lithio, potassio or magnesium halide derivative with a silyl compound of formula $R_xSi(NCY)_{4-x}$ wherein R is alkyl, aryl or aralkyl, Y is oxygen or sulphur and x has a value from 0 to 3 and subjecting the product to hydrolysis or alcoholysis. The reaction is conducted under anhydrous conditions preferably in an inert solvent for example a hydrocarbon solvent such as benzene, toluene or n-hexane. It is also stated in that patent specification that ethers, including cyclic ethers such as tetrahydrofuran should be avoided.

We have now surprisingly found that ethers can be used as solvents if the silyl reagent is modified to contain selected hydrocarbon groups and furthermore the yields are often better than with the solvents described in UK Specification No. 1463666. Our new process can also be used to prepare compounds related to those described in Patent Specification No. 1463666.

Accordingly this invention provides in one aspect, a process for preparing compounds of formula I

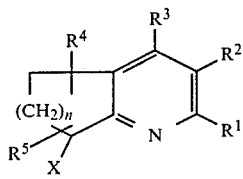

or acid addition salts thereof, wherein $R^1$, $R^2$, $R^3$, $R^4$ and $R^5$ are the same or different and represent hydrogen or alkyl, cycloalkyl, aralkyl, or aryl radicals, any of which radicals may be substituted, or $R^1$ and $R^2$ taken together, or $R^2$ and $R^3$ taken together, form a 5, 6 or 7 membered ring which may be saturated or unsaturated and substituted or unsubstituted, and when $R^1$ and $R^2$ form a ring the ring has the same number of carbon atoms as the ring carrying X, $R^4$ and $R^5$ may also represent alkoxy, n is 1, 2 or 3 and X is CN, $CONH_2$ or $CSNH_2$, which process comprises treating a compound of formula II

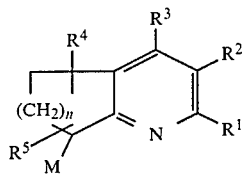

wherein $R^1$, $R^2$, $R^3$, $R^4$, $R^5$ and n are as defined in connection with formula I, and M is sodium, potassium, lithium, or MgHal, where Hal is chlorine, bromine or iodine, with a silyl compound of formula III, $R_x{}^aSi(NCY)_{4-x}$ wherein $R^a$ is alkyl, cycloalkyl, aralkyl, or aryl, at least one group $R^a$ being a branched chain alkyl, cycloalkyl, aryl, or branched chain aralkyl, Y is oxygen or sulphur, x has a value from 1 to 3, then subjecting the product to hydrolysis with the proviso that when a compound of formula I in which X is CN is desired the molar ratio of compound $R_x{}^aSi(NCY)_{4-x}$ to compound II is at least 2:1 and x is 3 and Y is S and if desired isolating the product as an acid addition salt.

If at least one $R^a$ is not t-alkyl then preferably at least two groups $R^a$ are selected from branched chain alkyl, cycloalkyl, aryl or branched chain aralkyl.

The compounds of formula I and II are, in general, known compounds which are described in UK Patent Specification Nos. 1463666, 1432378, 1463668, 1465651 and 1495993 or are analogous to compounds described therein. Compounds of formula II in which M is MgHal are also described in UK Pat. No. 1463665 or are analogous to compounds described therein. The compounds of formula I in which X is $CSNH_2$ are anti-ulcer agents which display anti-ulcer and/or anti-secretory activity in standard test procedures. The nitriles of formula I where X is CN are intermediates for the corresponding thioamides and usually also display anti-ulcer and/or anti-secretory activity. The amides of formula I in which X is $CONH_2$ are intermediates for the corresponding nitriles and thioamides.

The reaction medium for the process of the present invention preferably comprises an ether solvent eg., a dialkyl ether, wherein the alkyl group has from 1 to 6 carbon atoms, eg., diethyl ether, or a cyclic ether such as tetrahydrofuran or dioxan. The solvents described in UK Patent Specification No. 1463666 eg., hydrocarbons such as benzene and toluene may also be used. With some compounds of formula II eg., those containing, 5 and 7 membered rings (where n is 1 or 3) and some tetrahydroquinolines such as those having $R^3$ as an alkyl group the reagents of formula III often give better yields than the reagents specifically disclosed in No. 1463666 eg., trimethylsilyl isothiocyanate. Mixtures of solvents may be used eg., an ether/hydrocarbon such as tetrahydrofuran/hexane.

Preferably $R^a$ is an alkyl group of 1–10 carbon atoms and at least one group $R^a$ is a tertiary alkyl group eg., t-butyl or t-amyl. Preferably x is 3. Good results have been obtained with silyl compound of formula $R_3{}^aS-iNCY$ wherein one group $R^a$ is t-butyl and the other two are lower alkyl eg., t-butyldimethylsilyl isothiocyanate.

When any of $R^1$, $R^2$, $R^3$, $R^4$ or $R^5$ is an alkyl radical it is preferred that this is a lower alkyl radical of 1 to 6 carbon atoms which may have a straight or branched chain eg., methyl, ethyl, n- and iso-propyl and n-, s- and t-butyl. When $R^a$ is a lower alkyl radical it may be any of the values just discussed. When $R^4$ or $R^5$ is an alkoxy radical it is preferred that the radical is lower alkoxy in which the alkyl portion has 1 to 6 carbon atoms and is as defined above, for an alkyl radical.

When any of $R^1$, $R^2$, $R^3$, $R^4$, $R^5$ or $R^a$ is a cycloalkyl radical such radicals having from 4 to 8 carbon atoms in the ring are preferred eg., cyclobutyl, cyclopentyl or cyclohexyl. Such rings may be substituted by alkyl of 1 to 6 carbon atoms.

An aralkyl group may be an arylalkyl group in which the alkyl portion is as described herein for an alkyl group. Preferred aralkyl groups are those having from 7–12 carbon atoms.

When any of $R^1$, $R^2$, $R^3$, $R^4$, $R^5$ or $R^a$ is an aryl group it is preferably phenyl or substituted phenyl (substituted by e.g. alkyl, alkoxy, or trifluoromethyl).

Apart from the question of solvent, already discussed above the reaction may be carried out as described generally in UK Patent Specification No. 1463666. Conveniently the starting material of formula II is prepared in situ by reaction of a compound of formula II, wherein M is hydrogen with a suitable organometallic compound such as an alkyl, aryl or aralkyl lithium, sodium or potassium compound as described in UK Patent Specification No. 1432378 or using the modification described in UK Patent Specification No. 1463666, wherein a metal amide is reacted with a compound of formula II wherein M is hydrogen. The metal amide may be formed in situ and may be any of those described in UK Patent Specification No. 1463666 viz. an amide derived from a secondary amine such as a dialkylamine e.g. diethylamine, di-isopropylamine, ditertiary butylamine, di-n-decylamine, dicyclohexylamine, N-t-amyl-N-t-butylamine, N-isopropyl-N-cyclohexylamine, or N(1 ethylcyclohexyl)-1,1,3,3,-tetramethylbutylamine or a cyclic compound e.g. piperidine, or 2,2,6,6,tetramethylpiperidine. Alternatively any of the metal amides described in co-pending U.S. Ser. No. 472,787 filed 7th Mar. 1983 may be used. These metal amides have the formula IV

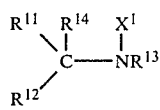

wherein $R^{14}$ is a straight or branched chain alkyl group of 1 to 6 carbon atoms or an aryl group, $R^{11}$ is hydrogen, aryl or a tertiary alkyl group of 4–6 carbon atoms, $R^{12}$ is aryl or a tertiary alkyl group of 4–6 carbon atoms, $R^{13}$ is a branched chain alkyl of 3 to 6 carbon atoms; $X^1$ is lithium, sodium or potassium. These metal amides are conveniently prepared by a novel process described in U.S. Ser. No. 472,787 namely reacting a compound of formula V.

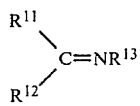

wherein $R^{11}$, $R^{12}$ and $R^{13}$ are as defined above with a metal alkyl $MR^{14}$ where $R^{14}$ is as defined above and M is lithium sodium or potassium, in an inert non-polar solvent to obtain a compound of formula IV.

A particularly preferred compound of formula IV is lithium N-t-butyl-N-(1-phenylpentyl)amide.

The starting compounds of formula II, wherein X is MgHal may be prepared by the general method described in UK Patent Specification No. 1463665. However, in our UK Patent Specification No. 1463666 it is said that the ether solvent has to be removed and the reaction with the silyl compound conducted in a different solvent. Since the process of the present invention can be conducted in ethers it is not usually necessary to remove the ether when the MgHal compound II has been prepared in an ether solvent. However it is usually desirable to reduce the volume of ether before reaction with the silyl compound.

The silyl compounds of formula III which are used in the process of the present invention may be prepared by reacting a thiocyanate, such as ammonium thiocyanate or a cyanate with a silyl halide eg., $R_3{}^aSiHal$ where $R^a$ is as defined above and Hal is chlorine bromine or iodine.

Some silyl compounds of formula III are novel. These novel compounds are included in the scope of the invention and are represented by formula IIIA, $R^bR^cR^dSiNCY$—wherein $R^b$ is a branched chain alkyl, cycloalkyl, aryl, branched chain aralkyl and $R^c$ and $R^d$ are selected from alkyl, cycloalkyl, aralkyl or aryl with the proviso that $R^c$ and $R^d$ are not the same radical as $R^b$, and Y is oxygen or sulphur. Processes for preparing compounds IIIA are also included.

Preferably $R^c$ and $R^d$ are alkyl radicals at least one and preferably both being n-alkyl radicals.

A particularly preferred compound of formula IIIA is t-butyldimethylsilyl isothiocyanate.

When it is desired to prepare nitriles by the above reaction instead of using 2 or more moles of compound $R_x{}^aSi(NCY)_{4-x}$ to compound II the reaction may be carried out by reacting 1 mol of compound $R_x{}^aSi(NCY)_{4-x}$ with compound II followed by addition of 1 or more mols of $R_x{}^aSiCl_{4-x}$ wherein $R^a$ and x are as defined previously. $R^a$ and x in this reagent need not be the same as $R^a$ and x in the reagent $R_x{}^aSi(NCY)_{4-x}$. A compound $R_x{}^aSiBr_{4-x}$ may be used instead of the corresponding chloride.

The following Examples illustrate the invention.

EXAMPLE 1

Preparation of silyl isothiocyanates

General Method

Ammonium thiocyanate (1.1 molar equivalents) in cyclohexane (100 ml) was refluxed with stirring under a Dean-Stark apparatus until water had been removed. The suspension was cooled and treated with a silyl chloride (50 g) and the mixture was heated at reflux with stirring until the reaction was complete (usually 24 hours). Precipitated ammonium chloride was removed by filtration and the product purified by distillation. In this manner were prepared the following:

| Silyl chloride | Silylisothiocyanate | bp/mm | Yield |
|---|---|---|---|
| (a) t-BuMe₂SiCl | t-BuMe₂SiNCS | 62°/16 | 93% |
| (b) i-Pr₃SiCl | i-Pr₃SiNCS | 125°/15 | 71% |
| (c) PhMe₂SiCl | PhMe₂SiNCS | 144°/15 | 80% |

EXAMPLE 2

5,6,7,8-Tetrahydro-3,8-dimethylquinoline-8-thiocarboxamide

A 1.55 molar solution of butyl lithium in hexane (12.9 ml, 20 mM) maintained below 10° was treated with a solution of 5,6,7,8-tetrahydro-3,8-dimethylquinoline (3.22 g, 20 mM) in tetrahydrofuran (10 ml). After 0.5 hours a 22% solution of t-butyldimethylsilyl isothiocyanate in benzene (13.7 g, 20 mM) was added dropwise. After a further 0.5 hours the reaction was quenched with water (100 ml.) then acidified (to pH1). After 1 hour the layers were separated, the aqueous layer basified (to pH9) and extracted with dichloromethane (2×50 ml). The organic extracts were dried and evaporated. Recrystallisation of the residue from toluene gave the title thioamide (3.3 g, 75%) mp. 160°-2°
(Found: C,65.45; H,7.2; N,12.9% $C_{12}H_{16}N_2S$ requires C,65.4; H,7.3; N,12.7%)

EXAMPLE 3

8-Cyano-5,6,7,8-tetrahydro-3,8-dimethylquinoline

A solution of 5,6,7,8-tetrahydro-8-lithio-3,8-dimethylquinoline (20 mM) was generated as described in Example 2 and allowed to react with t-butyldimethylsilyl isothiocyanate (20 mM) as described in Example 2. After 0.5 hours a solution of t-butyldimethylsilyl chloride (3.1 g, 20 mM) in THF (10 ml) was added and the mixture allowed to stand for 16 hours at ambient temperature. The reaction was quenched with 2N hydrochloric acid (50 ml). After 1 hour the aqueous layer was separated, basified (to pH9) and extracted with dichloromethane (2×50 ml) and the organic extracts were dried and evaporated. Kugelrohr distillation of the residue gave the nitrile title compound. (2.8 g, 75%) bp. 90°/0.01 mm (bath temp.)

(Found: C,77.1; H,8.1; N,14.5% $C_{12}H_{14}N_2$ requires: C,77.4; H,7.6; N,15.0%)

EXAMPLE 4

5,6,7,8-Tetrahydro-3-methylquinoline-8-thiocarboxamide

Following the procedure of Example 2, but using 5,6,7,8-tetrahydro-3-methylquinoline as starting material the title compound was obtained in 50% yield mp 149° C., identical with authentic material.

I claim:

1. A process for preparing compounds of formula I

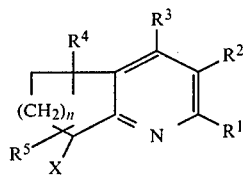

or acid addition salts thereof, wherein $R^1$, $R^2$, $R^3$, $R^4$ and $R^5$ are the same or different and represent hydrogen or alkyl of 1–6 carbon atoms, cycloalkyl of 4–8 carbon atoms, phenylalkyl of 7–12 carbon atoms or phenyl groups, any of which groups may be substituted by alkyl of 1–6 carbon atoms, alkoxy of 1–6 carbon atoms or trifluoromethyl; or $R^1$ and $R^2$ taken together, or $R^2$ and $R^3$ taken together, form a 5, 6 or 7 membered carbocyclic ring which may be saturated or unsaturated, and when $R^1$ and $R^2$ form a ring the ring has the same number of carbon atoms as the ring carrying X; $R^4$ and $R^5$ may also represent alkoxy of 1–6 carbon atoms; n is 1, 2 or 3 and X is CN, $CONH_2$ or $CSNH_2$; which process comprises treating, in a reaction medium comprising an ether solvent, a compound of formula II

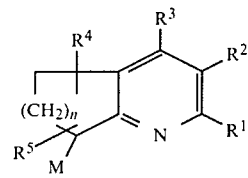

wherein $R^1$, $R^2$, $R^3$, $R^4$, $R^5$ and n are as defined in connection with formula I, and M is sodium, potassium, lithium, or MgHal, where Hal is chlorine, bromine or iodine, with a silyl compound of formula III, $R_x{}^aSi(NCY)_{4-x}$ wherein $R^a$ is alkyl of 1–10 carbon atoms, cycloalkyl of 4–8 carbon atoms, phenylalkyl of 7–12 carbon atoms or phenyl, at least one group $R^a$ being a branched chain alkyl of 3–10 carbon atoms, cycloalkyl of 4–6 carbon atoms, phenyl or branched chain phenylalkyl of 8–12 carbon atoms, Y is oxygen or sulphur, x has a value from 1 to 3, then subjecting the product to hydrolysis or alcoholysis with the proviso that when a compound of formula I in which X is CN is desired the molar ratio of compound $R_x{}^aSi(NCY)_{4-x}$ to compound II is at least 2:1 and x is 3 and Y is S and if desired isolating the product as an acid addition salt.

2. A process as claimed in claim 1, wherein the silyl compound III is $R_3{}^aSiNCY$ and at least one group $R^a$ is a t-alkyl group.

3. A process as claimed in claim 2, wherein one group $R^a$ in the compound of formula III is t-butyl and the other two are n-lower alkyl of 1–6 carbon atoms.

4. A process as claimed in claim 3, wherein the compound of formula III is t-butyldimethylsilyl isothiocyanate.

5. A process as claimed in claim 1, wherein the silyl compound III is $R_3{}^aSiNCY$ and at least two groups $R^a$ are selected from branched chain alkyl of 3–10 carbon atoms, cycloalkyl of 4–8 carbon atoms, phenyl or branched chain phenylalkyl groups of 8–12 carbon atoms.

6. A process as claimed in claim 1, wherein the compound of formula III is dimethylphenylsilyl isothiocyanate.

7. A process as claimed in claim 5, wherein the compound of formula III is tri-isopropylsilyl isothiocyanate.

8. A process as claimed in claim 1, wherein a compound of formula II is used in which $R^1$, $R^2$, $R^3$, $R^4$ and $R^5$ are selected from hydrogen and alkyl of 1–6 carbon atoms.

9. A process as claimed in claim 1, wherein the reaction medium comprises diethyl ether or a cyclic ether.

10. A process as claimed in claim 1, wherein the reaction medium comprises tetrahydrofuran.

11. A process as claimed in claim 10, wherein the reaction medium comprises tetrahydrofuran and a hydrocarbon solvent.

12. A process as claimed in claim 11, wherein the reaction medium comprises tetrahydrofuran and hexane.

* * * * *